US012558489B2

(12) United States Patent
Toporek et al.

(10) Patent No.: US 12,558,489 B2
(45) Date of Patent: Feb. 24, 2026

(54) INJECTION DEVICE

(71) Applicant: SANOFI, Paris (FR)

(72) Inventors: Maurice Toporek, Frankfurt am Main (DE); Markus Ploch, Frankfurt am Main (DE); Stefan Blancke, Frankfurt am Main (DE)

(73) Assignee: SANOFI, Paris (FR)

( * ) Notice: Subject to any disclaimer, the term of this patent is extended or adjusted under 35 U.S.C. 154(b) by 1476 days.

(21) Appl. No.: 16/982,684

(22) PCT Filed: Mar. 25, 2019

(86) PCT No.: PCT/EP2019/057390
§ 371 (c)(1),
(2) Date: Sep. 21, 2020

(87) PCT Pub. No.: WO2019/185516
PCT Pub. Date: Oct. 3, 2019

(65) Prior Publication Data
US 2021/0290856 A1 Sep. 23, 2021

(30) Foreign Application Priority Data
Mar. 28, 2018 (EP) .................................... 18305344

(51) Int. Cl.
*A61M 5/315* (2006.01)
(52) U.S. Cl.
CPC ...... *A61M 5/31566* (2013.01); *A61M 5/3155* (2013.01); *A61M 5/31563* (2013.01);
(Continued)
(58) Field of Classification Search
CPC .......... A61M 5/31568; A61M 5/31565; A61M 5/31533; A61M 5/31525;
(Continued)

(56) References Cited

U.S. PATENT DOCUMENTS

| | | | | |
|---|---|---|---|---|
| 10,518,035 B2 * | 12/2019 | Hirschel | ........... | A61M 5/31551 |
| 2011/0270214 A1 * | 11/2011 | Jorgensen | ......... | A61M 5/31551 |
| | | | | 604/207 |

(Continued)

FOREIGN PATENT DOCUMENTS

| | | |
|---|---|---|
| CN | 104203315 | 12/2014 |
| CN | 104394916 | 3/2015 |

(Continued)

OTHER PUBLICATIONS

International Preliminary Report on Patentability in International Appln. No. PCT/EP2019/057390, dated Sep. 29, 2020, 7 pages.
(Continued)

*Primary Examiner* — Kevin C Sirmons
*Assistant Examiner* — Antarius S Daniel
(74) *Attorney, Agent, or Firm* — Bond, Schoeneck & King, PLLC

(57) ABSTRACT

An injection device comprises a housing with a receptacle for the product, a dosing mechanism for setting a product dosage, a dispensing mechanism for dispensing the product, at least one sleeve, which is rotatable relative to the housing in order to eject the set product dosage, and a stop wheel coupled to the at least one sleeve such that the stop wheel is rotatable relative to the housing and the at least one sleeve for setting a product dosage and together with the at least one sleeve relative to the housing in order to eject the set product dosage. The device further comprises a first detector for detecting movement of the stop wheel relative to the housing and/or the at least one sleeve and a data processing unit connected to the first detector reading, storing, processing, transmitting, and/or displaying signals received from the first detector.

19 Claims, 2 Drawing Sheets

Specification includes a Sequence Listing.

(52) U.S. Cl.
CPC ... *A61M 5/3158* (2013.01); *A61M 2205/3306* (2013.01); *A61M 2205/3317* (2013.01); *A61M 2205/3584* (2013.01); *A61M 2205/50* (2013.01); *A61M 2205/581* (2013.01); *A61M 2205/582* (2013.01)

(58) Field of Classification Search
CPC .... A61M 2005/3126; A61M 2205/332; A61M 2205/3317; A61M 5/31551; A61M 5/31585; A61M 5/31528
See application file for complete search history.

(56) References Cited

U.S. PATENT DOCUMENTS

| | | | | |
|---|---|---|---|---|
| 2012/0165751 A1* | 6/2012 | Plumptre | .......... | A61M 5/31551 |
| | | | | 604/207 |
| 2013/0204202 A1* | 8/2013 | Trombly | .......... | A61M 5/16877 |
| | | | | 604/207 |
| 2015/0343152 A1* | 12/2015 | Butler | ............... | A61M 5/31585 |
| | | | | 604/207 |
| 2015/0367077 A1* | 12/2015 | Plambech | ......... | A61M 5/31528 |
| | | | | 604/211 |
| 2018/0050155 A1 | 2/2018 | Avery et al. | | |
| 2018/0126088 A1* | 5/2018 | Radmer | .............. | A61M 5/3158 |
| 2019/0015596 A1* | 1/2019 | Saint | ...................... | G16H 50/20 |
| 2019/0217016 A1* | 7/2019 | Rehbein | .............. | A61M 5/2033 |
| 2020/0360614 A1* | 11/2020 | Schabbach | ......... | G01D 5/34723 |

FOREIGN PATENT DOCUMENTS

| | | |
|---|---|---|
| CN | 107735128 | 2/2018 |
| EP | 2437829 | 4/2012 |
| EP | 2814547 | 12/2014 |
| EP | 2814547 B1 | 7/2015 |
| JP | 2014-517734 | 7/2014 |
| JP | 2015-506771 | 3/2015 |
| JP | 2015-516242 | 6/2015 |
| WO | WO 2010/139645 | 12/2010 |
| WO | WO 2011/117212 | 9/2011 |
| WO | WO 2012/140097 | 10/2012 |
| WO | WO 2013/120778 | 8/2013 |
| WO | WO 2013/170392 | 11/2013 |
| WO | WO 2014/033197 | 3/2014 |
| WO | WO 2014/117944 | 8/2014 |
| WO | WO 2016/001304 | 1/2016 |
| WO | WO 2016/016184 | 2/2016 |
| WO | WO 2017/005878 | 1/2017 |
| WO | WO 2017/134131 | 8/2017 |

OTHER PUBLICATIONS

PCT International Search Report and Written Opinion in International Appln. No. PCT/EP2019/057390, dated Jun. 26, 2019, 10 pages.

* cited by examiner

Fig. 2
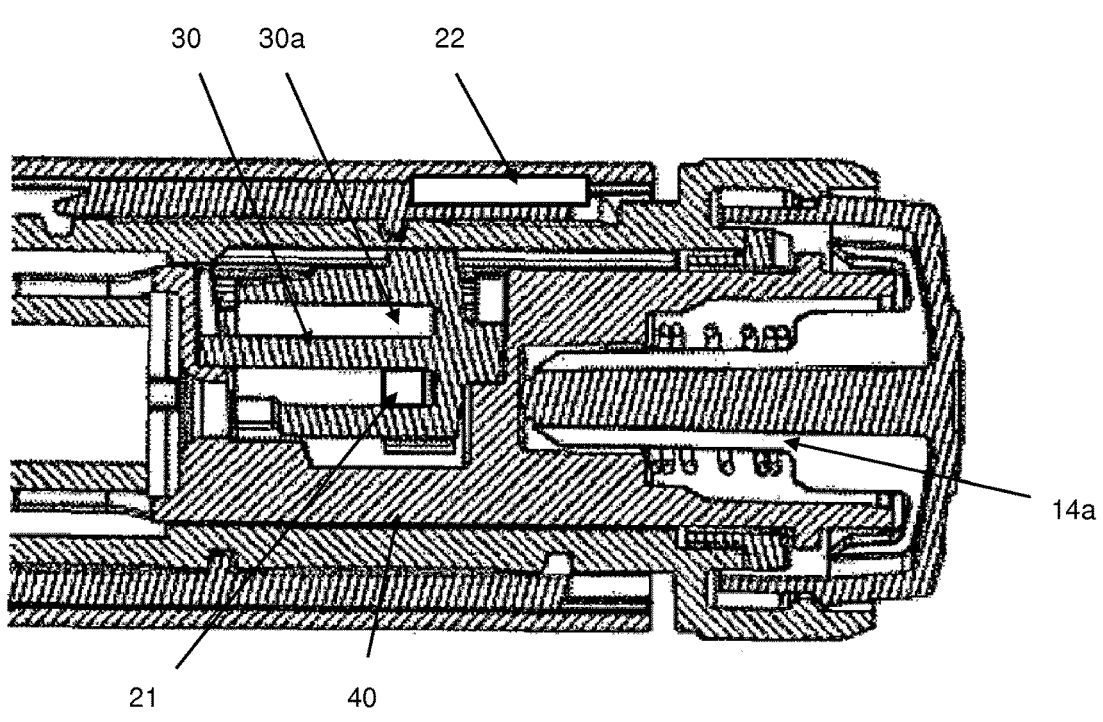
Fig. 3
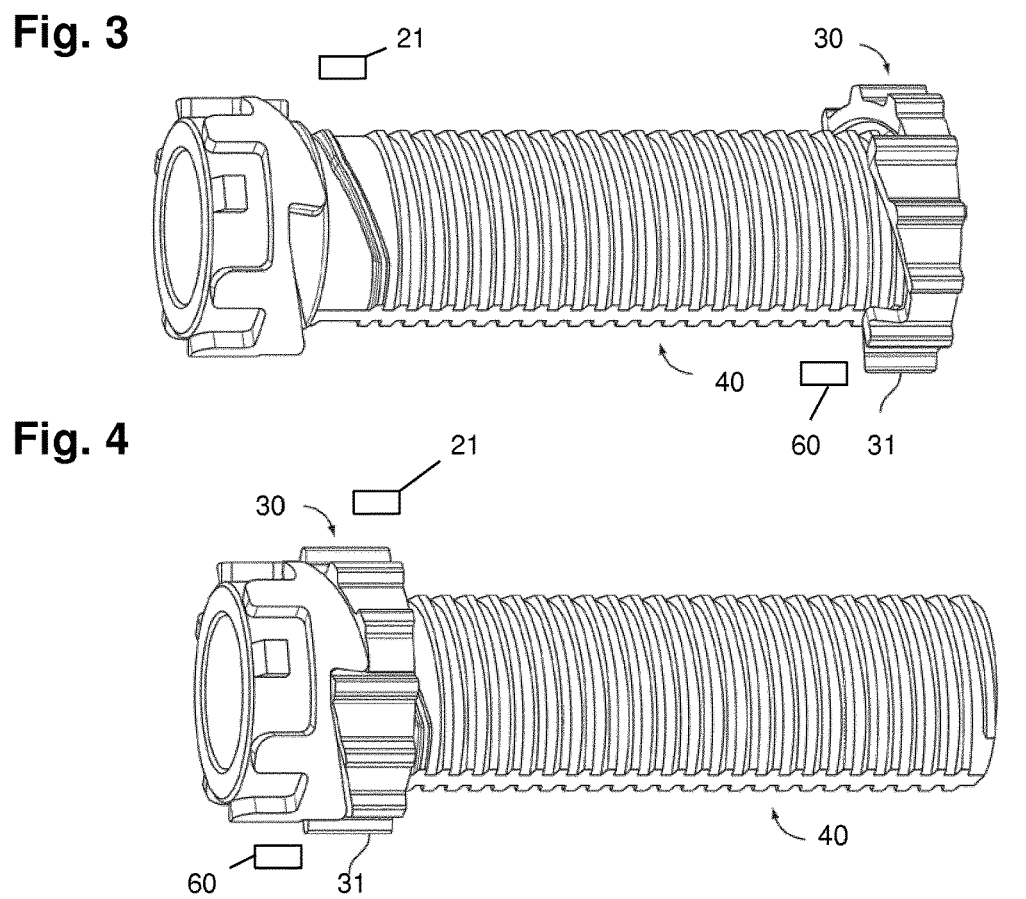
Fig. 4

SEQUENCE LISTING

```
<160> NUMBER OF SEQ ID NOS: 41

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
```

```
<220> FEATURE:
<223> OTHER INFORMATION: H-(Lys)4-des Pro36, des Pro37 Exendin-4(1-39)-
      NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-
      NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
```

```
<223> OTHER INFORMATION: des Pro36 [IsoAsp28] Exendin-4(1-39)
<220> FEATURE:
<221> NAME/KEY: MOD_RES
<222> LOCATION: (27)..(27)
<223> OTHER INFORMATION: X = isoaspartate
<220> FEATURE:
<221> NAME/KEY: misc_feature
<222> LOCATION: (28)..(28)
<223> OTHER INFORMATION: Xaa can be any naturally occurring amino acid

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MOD_RES
<222> LOCATION: (14)..(14)
<223> OTHER INFORMATION: X = methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (27)..(27)
<223> OTHER INFORMATION: X = isoaspartate
<220> FEATURE:
<221> NAME/KEY: misc_feature
<222> LOCATION: (28)..(28)
<223> OTHER INFORMATION: Xaa can be any naturally occurring amino acid

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
```

-continued

```
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MOD_RES
<222> LOCATION: (25)..(25)
<223> OTHER INFORMATION: X = tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MOD_RES
<222> LOCATION: (25)..(25)
<223> OTHER INFORMATION: X = tryptophan dioxide
<220> FEATURE:
<221> NAME/KEY: MOD_RES
<222> LOCATION: (28)..(28)
<223> OTHER INFORMATION: X = isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28] Exendin-
      4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
```

```
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan dioxide
<220> FEATURE:
<221> NAME/KEY: MOD_RES
<222> LOCATION: (28)..(28)
<223> OTHER INFORMATION: X = isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28] Exendin-4(1-39)-
      Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
      NH2

<400> SEQUENCE: 15
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35
```

```
<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28] Exendin-
      4(1-39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40
```

```
<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

<400> SEQUENCE: 17

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40
```

```
<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28] Exendin-
      4(1-39)-(Lys)6-NH2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40
```

```
<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2
```

-continued

```
<400> SEQUENCE: 19

Lys Lys Lys Lys Lys Lys His Gly Glu Gly Thr Phe Thr Ser Asp Leu
1               5               10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20

Asn Glu Glu Glu Glu Glu His Gly Glu Gly Thr Phe Thr Ser Asp Leu
1               5               10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28] Exendin-
      4(1-39)-Lys6-NH2
<220> FEATURE:
<221> NAME/KEY: MOD_RES
<222> LOCATION: (31)..(31)
<223> OTHER INFORMATION: X = tryptophan dioxide

<400> SEQUENCE: 21

Lys Lys Lys Lys Lys Lys His Gly Glu Gly Thr Phe Thr Ser Asp Leu
1               5               10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MOD_RES
<222> LOCATION: (25)..(25)
<223> OTHER INFORMATION: X = tryptophan dioxide

<400> SEQUENCE: 22
```

-continued

```
His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
                20                  25                  30

Gly Ala Pro Pro Pro Ser
            35
```

```
<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MOD_RES
<222> LOCATION: (31)..(31)
<223> OTHER INFORMATION: X = tryptophan dioxide

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
                20                  25                  30

Lys Asp Gly Gly Pro Ser Ser Gly Ala Pro Pro Ser
            35                  40
```

```
<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-NH2
<220> FEATURE:
<221> NAME/KEY: MOD_RES
<222> LOCATION: (31)..(31)
<223> OTHER INFORMATION: X = tryptophan dioxide

<400> SEQUENCE: 24

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
                20                  25                  30

Lys Asp Gly Gly Pro Ser Ser Gly Ala Pro Pro Ser
            35                  40
```

```
<210> SEQ ID NO 25
<211> LENGTH: 44
<212> TYPE: PRT
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MOD_RES
<222> LOCATION: (25)..(25)
<223> OTHER INFORMATION: X = tryptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
                20                  25                  30

Ser Gly Ala Pro Pro Ser Lys Lys Lys Lys Lys Lys
```

-continued

```
              35                      40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MOD_RES
<222> LOCATION: (31)..(31)
<223> OTHER INFORMATION: X = tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MOD_RES
<222> LOCATION: (31)..(31)
<223> OTHER INFORMATION: X = tryptophan dioxide

<400> SEQUENCE: 27

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 50
<212> TYPE: PRT
<213> ORGANISM: Artificial Sequence
<220> FEATURE:
<223> OTHER INFORMATION: H-(Lys)6-des Pro36 [Met(O)14, Asp28] Exendin-
      4(1-39)-Lys6-NH2
<220> FEATURE:
<221> NAME/KEY: MOD_RES
<222> LOCATION: (20)..(20)
<223> OTHER INFORMATION: X = methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45
```

```
Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38 Exendin-
      4(1-39)-NH2

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 30

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
```

```
          Exendin-4(1-39)-(Lys)6-NH2
<220> FEATURE:
<221> NAME/KEY: MOD_RES
<222> LOCATION: (14)..(14)
<223> OTHER INFORMATION: X = methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
                20                  25                  30

Ser Gly Ala Pro Pro Ser Lys Lys Lys Lys Lys Lys
        35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
<220> FEATURE:
<221> NAME/KEY: MOD_RES
<222> LOCATION: (20)..(20)
<223> OTHER INFORMATION: X = methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
        35                  40                  45

Lys Lys
    50

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MOD_RES
<222> LOCATION: (20)..(20)
<223> OTHER INFORMATION: X = methionine oxide

<400> SEQUENCE: 34

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
```

```
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan oxide

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 37
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 37

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 38
<211> LENGTH: 44
<212> TYPE: PRT
```

-continued

```
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide

<400> SEQUENCE: 38

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 39
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan oxide

<400> SEQUENCE: 39

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 40
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide

<400> SEQUENCE: 40

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45
```

-continued

```
Lys Lys
    50

<210> SEQ ID NO 41
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide

<400> SEQUENCE: 41

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```

INJECTION DEVICE

CROSS REFERENCE TO RELATED APPLICATIONS

The present application is the national stage entry of International Patent Application No. PCT/EP2019/057390, filed on Mar. 25, 2019, and claims priority to Application No. EP 18305344.6, filed on Mar. 28, 2018, the disclosures of which are incorporated herein by reference.

TECHNICAL FIELD

The present disclosure is generally directed to an injection device, i.e. a drug delivery device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

An injection device comprising a housing with a receptacle for the product, a dosing mechanism for setting a product dosage to be administered and for displaying the set product dosage and a dispensing mechanism for dispensing the product is known e.g. from EP 2 814 547 B1 which discloses a manually driven device or from WO 2014/117944 A1, WO 2016/016184 A1 or WO 2017/134131 A1 which disclose spring driven devices.

While some of these known devices are provided with a feedback mechanism for generating a feedback suitable for indicating e.g. the action of dose dispensing by providing a non-visual feedback signal to a user, it may be desirable for some applications to get such information in a different manner, for example in a way enabling storing and processing this information. Further, it may be desirable to receive information on the state of the device, i.e. whether the device is in a dispensing mode or the dose setting mode.

SUMMARY

Certain aspects provide an injection device or a drug delivery device providing additional information to users regarding the actual operation mode of the device.

An injection device according to one aspect comprises a housing with a receptacle for the product, a dosing mechanism for setting a product dosage to be administered and for displaying the set product dosage and a dispensing mechanism for dispensing the product. The dispensing mechanism of the device may comprise a piston rod, which is moveable relative to the housing in a dispensing direction in order to eject the set product dosage in a dispensing stroke corresponding to the set product dosage, at least one sleeve, which is movable relative to the housing in order to eject the set product dosage, and a stop wheel, e.g. an end-of-content stop wheel, coupled to the at least one sleeve such that the stop wheel is movable relative to the housing and the at least one sleeve for setting a product dosage and together with the at least one sleeve relative to the housing in order to eject the set product dosage. Detecting movements of one or more component parts of the injection device may be used to identify the actual operation mode of the device.

For example, the device may further comprise a first detector for detecting movement of the stop wheel relative to the housing and/or the at least one sleeve and a data processing unit connected to the first detector for reading, storing, processing, transmitting and/or displaying signals received from the first detector. In more detail, the first detector and the data processing unit may be adapted to detect start and stop of a rotational movement of the stop wheel, the angle of rotation the rotational movement of the stop wheel and the direction of the rotational movement of the stop wheel. Detecting start and stop of the rotational movement is indicative of the stop wheel being in motion or not. Further, the angle of rotation is indicative of the size of a dose which is selected and/or a dispensed by the drug delivery device. The direction of the rotational movement is indicative of the operation mode of the device, for example if the stop wheel rotates in a first direction during dose setting and rotates in a second, opposite direction during dose correction and/or dose dispensing. Summarizing, detecting the movement of the stop wheel provides the required information for giving a feedback to the user regarding the operation mode of the device. According to an embodiment, the at least one detector and/or the data processing unit may be provided integrated within the injection device or, in an alternative embodiment, in a separate external unit which may be permanently or detachably connected to the injection device.

In an embodiment of the invention, the at least one sleeve may be rotatable relative to the housing in order to eject the set product dosage and the stop wheel may be rotatable relative to the housing and the at least one sleeve during setting a product dosage and together with the at least one sleeve relative to the housing during ejection of the set product dosage. In a further embodiment of the invention, the at least one sleeve may be axially displaceable, e.g. parallel to the direction of axial movement of the piston rod, relative to the housing in order to eject the set product dosage and the stop wheel may be axially displaceable, e.g. parallel to the direction of axial movement of the piston rod, relative to the housing and the at least one sleeve during setting a product dosage and together with the at least one sleeve relative to the housing during ejection of the set product dosage.

The stop wheel may have the form of a gear wheel and/or may have the form of a ring, a sleeve or a nut.

The above mentioned information may be used in conjunction with additional information, for example with respect to the content of the drug provided in the receptacle prior to the first use. The data processing unit may be adapted to provide information about the remaining content in the receptacle, the dose size and/or amount of product ejected from the device by the dispensing mechanism and/or the maximum dose set by the dosing mechanism based on a rotation protocol containing data received from the first detector, for example in conjunction with additional information.

According to a preferred embodiment, the injection device is substantially the device as disclosed in EP 2 814 547 B1 with a modified stop wheel. In EP 2 814 547 B1 the stop wheel comprises a cavity such that the stop wheel may be modified by providing the first detector and/or the data processing unit in the cavity of the stop wheel. In more detail, the stop wheel may comprise an outer skirt with ribs for engaging corresponding inner ribs of a number sleeve of the dosing mechanism of the device and an elastically deformable shaft which is rotatably mounted in the at least one sleeve, wherein the cavity is an annular space between the outer skirt and the elastically deformable shaft. This cavity as provided in the stop wheel of EP 2 814 547 B1 is especially suitable for receiving and housing the first detector and/or the data processing unit without requiring adaption of the further component parts of the device. In addition, it is possible to achieve all the functions and benefits of the device as described in EP 2 814 547 B1. A detector or a sensor of the detector located within the stop wheel may be adapted to detect rotation of the stop wheel about its rotation axis.

As an alternative, the injection device may be substantially the device as disclosed in WO 2014/117944 A1 having an end of content ring interposed between a tubular clutch and a drive tube. The end of content ring forms a stop wheel rotating at relative to the tubular clutch during dose setting and rotating together with the tubular clutch and the drive tube during dose dispensing. At the least of the first detector may be provided within the end of content ring, e.g. by providing a cavity in the end of content ring for receiving the first detector and/or the data processing unit. Still further alternatives include using one of the end of content elements of WO 2016/016184 A1 or WO 2017/134131 A1 as the stop wheel according to certain aspects.

According to a still further embodiment, the injection device may be substantially the device as disclosed in EP 2 437 829 B1 having a stop wheel in the form of a last dose nut which is rotationally constrained to the housing by means of a splined interface and which is in threaded engagement with a shaft having a rotational end stop limiting movement of the last dose nut.

The first detector may comprise at least one of an optical sensor, a capacitive sensor, an inductive sensor and a magnetic sensor, for example a magnetic rotation encoder (quadrature encoder). This may require that the stop wheel or other component parts of the injection device comprises at least a portion of a material permitting detection by an inductive sensor or a magnetic sensor. For example, the first detector may comprise a vibrating structure microelectromechanical systems (MEMS) gyroscope. Such vibrating structure gyroscopes which are also known as Coriolis vibratory gyroscopes are small enough to be implemented into component parts of an injection device without requiring significant building space. The detector may comprise one or more sensors integrating a gyroscope and at least one accelerometer into one detector unit.

While the first detector is sufficient to obtain information regarding the, e.g. rotational, movement of the stop wheel or other component parts of the injection device, it may be desirable to obtain additional information from the injection device. This may require that the injection device further comprises a second detector for detecting rotational movement of component parts of the injection device, e.g. of the at least one sleeve or a component part coupled to the at least one sleeve. The data processing unit may be connected to the second detector for reading, storing, processing, transmitting and/or displaying signals received from the second detector. The second detector may be of the same type as the first detector or may be a different type of detector. For example, the second detector may comprise at least one of an optical sensor, a capacitive sensor, an inductive sensor, a magnetic sensor and a vibrating structure microelectromechanical systems (MEMS) gyroscope.

The data processing unit may be adapted to provide information about the device being in its dose setting mode, its dose correction mode or its dose dispensing mode based on data received from the first detector and the second detector. In a pen-type injection device there is at least one component part, typically several component parts, rotating when the device is in operation, i.e. during setting or dispensing a dose. To detect the start and the end of the injection, the rotation of the stop wheel relative to the body or housing may be detected. The rotation stops with the end of the injection. However, it may be required to differentiate between dose dialing and injection. In an injection device according to another aspect, which may be a similar to the device of EP 2 814 547 B1, during dialing the rotation of the at least one sleeve, for example a coupling sleeve, and the stop wheel are equal. On the other hand, during injection the at least one sleeve, for example the coupling sleeve, is rotating while the stop wheel is not rotating relative to the at least one sleeve. For example, in the device of EP 2 814 547 B1, the stop wheel, the coupling sleeve and a dosing sleeve rotates together relative to the body or housing during dose dispensing. Such relative movements may be detected by a magnetic or inductive sensor.

The second detector may be provided in or on the housing of the injection device or alternatively in or on a button provided to trigger or effects dose dispensing. The button may be provided with portions which axially overlap with the at least one sleeve only in certain modes of the device, for example if the button is fully depressed during dose dispensing. This relative axial movement of the button with respect to the at least one sleeve may be used for detecting movement of the at least one sleeve by the second detector, e.g. the second detector may be activated and de-activated by this axial movement or detection of the rotation of the at least one sleeve may require that at least a portion of the button carrying the second detector is located axially within the at least one sleeve.

The data processing unit may be provided within the housing of the injection device. For example, the data processing unit and the first and second detector may be permanently provided within the housing of the injection device. This includes embodiments in which the data processing unit is connected to at least one of the first and second detector by wire. As an alternative, the data processing unit may be detachable from the housing and/or may be connected to at least one of the first and second detector by means of a wireless connection. In other words, the data processing unit may be an add-on device which may be attached to the housing and removed from the housing. Examples for wireless communication between the data processing unit and at least one detector may include communication via a near field communication (NFC) or via Bluetooth (BT).

Further, the data processing unit may be adapted to send data to and/or receive data from a separate data processing and/or display device, e.g. portable handheld electronic devices, via a near field communication (NFC) or via Bluetooth (BT). The data may be queried after each use (injection) and read out or an add-on device could read, process and store the data and send a rotation protocol via to another device for further processing. The add-on device may alternatively transmit unprocessed data.

The at least one sleeve may be a component part which is in direct engagement with the piston rod. For example, the at least one sleeve may be a drive sleeve which is splined to the piston rod or which is in threaded engagement with the piston rod. However, as an alternative, the at least one sleeve may be a component part which is indirectly coupled to the piston rod, for example with a clutch or a transmission element interposed between the at least one sleeve and the piston rod. The at least one sleeve may be permanently coupled to the piston rod or may be selectively coupled to the piston rod only in a certain mode of the injection device, for example during dose dispensing.

The injection device may comprise two sleeves, which are rotatable relative to the housing in order to eject the set product dosage and which are rotationally constrained relative to each other but displaceable relative to each other in the dispensing direction. The second detector may detect actuation, i.e. rotation, of one of these sleeves or of both sleeves.

The injection device may be provided with at least one clicker mechanism for generating a feedback signal during movement of component parts of the device, e.g. during dose setting, dose correcting, dose dispensing and/or resetting of the device. For example, the at least one sleeve is provided with a clicker mechanism for generating a feedback signal during rotational movement of the at least one sleeve relative to the housing during dose dispensing.

The injection device typically comprises a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4 (1-39); or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF FIGURES

Non-limiting, exemplary embodiments of the invention will now be described with reference to the accompanying drawings, in which:

FIG. 2 shows a sectional view of a detail of the embodiment of FIG. 1;

FIG. 3 shows components of a further embodiment of an injection device in a first position relative to each other; and FIG. 4 shows the component parts of FIG. 3 in a second position relative to each other.

DETAILED DESCRIPTION

Figure 1:
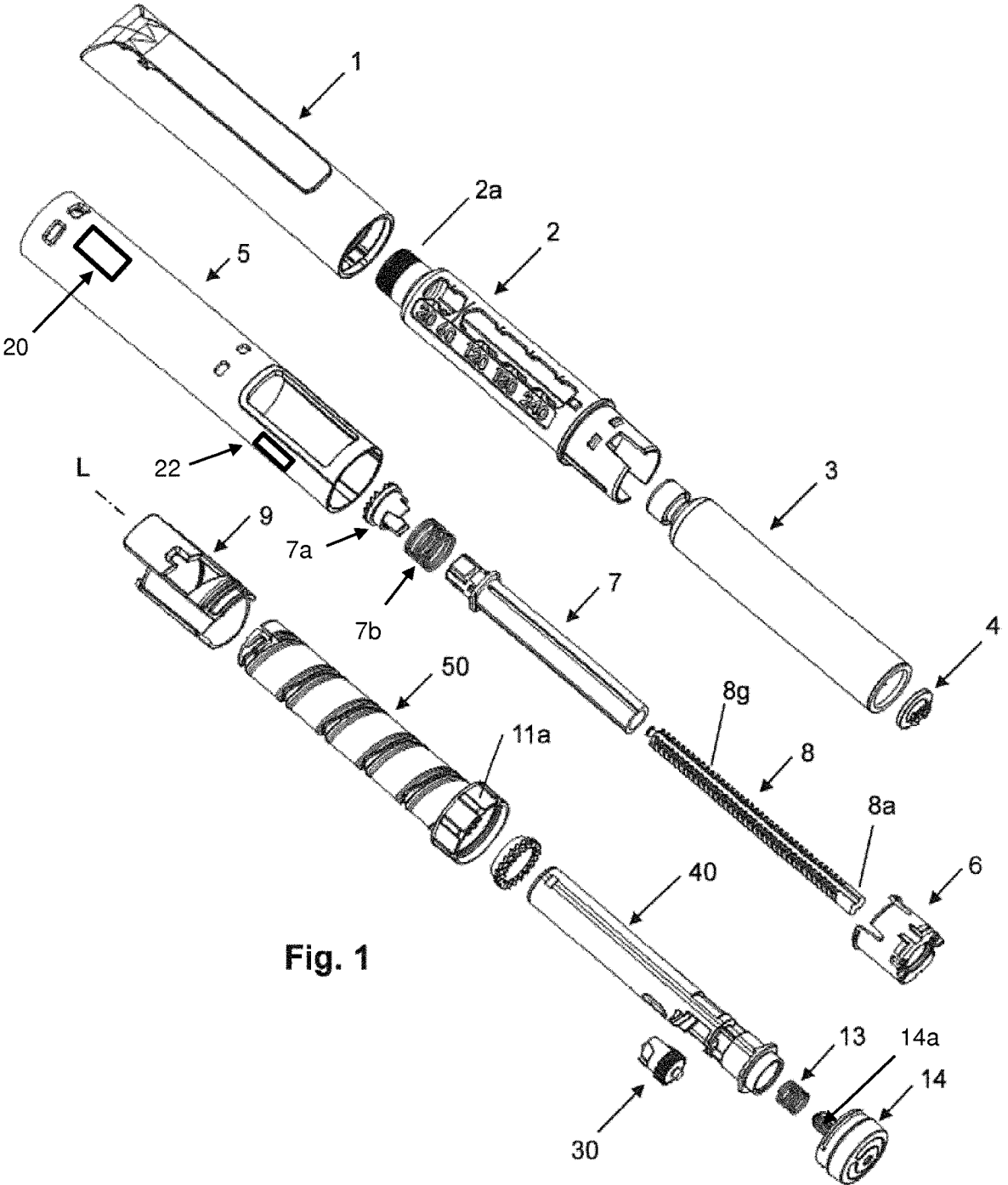
FIG. 1 shows an exploded view of the individual parts of an embodiment of an injection device.

FIG. 1 shows an exploded view of the individual parts of an embodiment of an injection device. This embodiment is designed as a so-called single-use pen. That is to say, the injection device is issued to the user fully assembled, i.e., with product to be administered.

The typical course of the injection process may be as follows: the user removes the protective cap 1 from the injection device and mounts an injection needle (not shown) on the needle holder 2a of a receptacle 2. Now the dosage can be adjusted via the rotary knob 11a. For this purpose, the rotary knob 11a is turned so that the dosing sleeve 50, which forms a dosing mechanism or is part of a dosing mechanism, is screwed out of the injection device. The dosing sleeve 50 is screwed out of the injection device until the desired dosage is displayed in the window of the threaded sleeve 9. If an excessively high dosage is inadvertently set, the dosage can be corrected by turning the rotary knob in the opposite direction, whereby the dosing sleeve 50 is screwed back into the housing. The dosing device limits the maximum adjustable dosage to a predetermined value. If there is an attempt to screw the dosing sleeve out of the housing past this value, a radial limit stop on the dosing sleeve 50 and a counter-limit stop on the threaded sleeve 9 prevent further rotation by mutual interaction. During the dosing and correction movements, the dosing sleeve 50 rotates relative to the coupling sleeve 40. The coupling sleeve 40 is held rotationally fixedly in a form fit or friction fit against the housing 5 by a reverse rotation lock, for example by means of a toothed ring 7a rotationally fixed to the threaded nut 7 and biased axially towards a corresponding set of ratchet teeth on an inner surface of the housing 5 by means of a spring 7b. This ratchet between the housing 5 and the threaded nut 7 may form a clicker generating an audible and/or tactile feedback during dose dispensing as the teeth of ring 7a slip over the corresponding teeth of housing 5.

The coupling sleeve 40 is permanently rotationally locked to the axially stationary threaded nut 7 by splines permitting relative axial movement between the coupling sleeve 40 which is axially entrained by the dosing sleeve 50 and the stationary threaded nut 7. The threaded nut 7 may be retained in the housing 5 by means of an insert 6 holding the threaded nut 7 against the bias of spring 7b. A toothed ring is shown in FIG. 1 which is interposed between rotary knob 11a and a flange on coupling sleeve 40 such that relative rotation of the dosing sleeve 50 and the coupling sleeve 40 is permitted during dose setting.

If the desired dosage has been set, the injection needle can be inserted at the intended position on the body of the user. Then the user pushes the ejection button 14 in the distal axial direction against the bias of spring 13 which is interposed between button 14 and coupling sleeve 40. This axial movement blocks a relative rotation between the coupling sleeve 40 and the dosing sleeve 50 by means of the toothed ring. In case of further pressure in the distal axial direction, the dosing sleeve begins to move back into the housing in a screwing motion. Because of the established rotational lock between the dosing sleeve 50 and the coupling sleeve 40, the coupling sleeve 40 carries out the same movement as the dosing sleeve 50. Because the coupling sleeve 40 is permanently rotationally locked to the axially stationary threaded nut 7, the rotational movement of the dosing sleeve 50 is transmitted to the threaded nut 7. No axial forces are transmitted to the threaded nut 7, because the coupling sleeve 40 is mounted axially movably on the threaded nut 7. Thus, the rotating threaded nut 7 produces an axial movement of the threaded piston rod 8 in the distal direction, wherein the latter is guided axially and locked rotationally in the housing 5 by means of splines 8*a* and is in threaded engagement with threaded nut 7 by means of an external thread 8*g*. The flange 4 acts on the plug of the cartridge 3 and pushes it, corresponding to the displacement of the threaded piston rod 8 in the distal direction as well, wherein the previously set dosage can be ejected or administered. At the end of the administration, when the dosing sleeve has been completely screwed back into the housing, radial stops on the dosing sleeve 50 and the threaded sleeve 9 prevent further ejection and overrotation of the dosing device.

The embodiment of FIG. 1 shows an optional limiting device which ensures that the most recently set dosage can be completely ejected or injected. For this purpose, the dosing sleeve 50 has a coaxially applied inner toothing and the coupling sleeve 40 has a lateral cutout in which the stop wheel 30 is inserted. The dosing sleeve 50 has a first stop means and the stop wheel 30 has a second stop means, wherein the stop wheel 30 follows movements of the dosing sleeve 50 during dosing movements with a defined transmission ratio, wherein the stop wheel 30 does not move relative to the dosing sleeve 50 during administration processes, wherein the first stop means and the second stop means each describe a path curve by their movements in such a manner that the two path curves intersect in at least one point or come so close together that the stop means contact one another in a stop position, whereby a blocking of the movement of the stop wheel 30 and the dosing sleeve 50 relative to each other during dosing movements can be effected, and wherein the respective path curves described by the first and second stop means are closed and can be run through preferably multiple times by the first stop means, by the second stop means or by both stop means until the stop means contact one another at the stop position. The function of the limiting device is described in EP 2 814 547 B1 in more detail.

The embodiment of FIG. 1 further shows a data processing unit 20 connected to a first detector 21 and a second detector 22 for reading data responsive to signals received from the first and second detectors 21, 22. The data processing unit 20 is depicted as a component part being disposed on the outer surface of the housing 5. It may be permanently attached to the housing 5 or may be an integral part thereof or may be a separate, detachable unit. The data processing unit 20 may comprise a power supply and a PCB suitable for e.g. data processing, data storing and/or display of information.

The first detector 21 is disposed in the stop wheel 30. In more detail FIG. 2 depicts the first detector 21 located in an annular cavity 30*a* of the stop wheel 30 which is provided interposed between a central shaft of the stop wheel 30 and an outer skirt of the stop wheel 30.

In the depicted embodiment, the first detector may be a magnetic rotation encoder (quadrature), a vibrating structure microelectromechanical systems (MEMS) gyroscope or a combination of an MEMS gyroscope and an accelerometer. These small size devices may be easily integrated into the cavity 30*a* of the stop wheel 30. If required the cavity 30*a* may be enlarged. Generally, gyroscopes measure rotational motion. MEMS (microelectromechanical system) gyroscopes are small, inexpensive sensors that measure angular velocity. The units of angular velocity are measured in degrees per second (°/s) or revolutions per second (RPS). Hence when determining the duration of the measurement the rotation angle can be determined that provides information about the dose size.

The optional second detector 22 is disposed in or on the housing 5 at a position suitable for detecting rotational movement of the coupling sleeve 40, preferably irrespective of the axial position of the coupling sleeve, e.g. at or near the proximal end of housing 5. As an alternative to the depicted embodiment where the second detector 22 is arranged on an inner side of housing 5, the second detector 22 may be located on the outer side of housing 5 or on threaded sleeve 6. Still further, the second detector 22 may be provided in or on the button 14, for example on a stem 14*a* of the button.

For example, the coupling sleeve 40 may be provided with markings detectable by an optical sensor as second detector 22 if the dosing sleeve 50 is at least partially transparent or translucent or provided with a window or the coupling sleeve 40 may be provided at least partially with a metallic material wherein rotation of this metallic portion is detectable by a sensor forming the second detector 22. It will be understood that as an alternative to detecting rotation of the coupling sleeve 40 rotation of threaded nut 7 and/or rotation of the toothed ring 7*a* may be detected. As an alternative, the second detector may comprise an acoustical sensor detecting the clicks generated during dose dispensing by the ratchet, i.e. by the teeth of ring 7*a* slipping over the corresponding teeth inside the housing 5.

During dialling (dose setting) the stop wheel 30 rotates driven by the rotating dosing sleeve 50 relative to and within the coupling sleeve 40 which is rotationally constrained to the housing. However, during injection the coupling sleeve 40 is rotationally coupled to the dosing sleeve 50 such that the stop wheel 30 performs a common rotational movement with the dosing sleeve 50 and the coupling sleeve 40. The relative movements may be detected by the first and/or second detector(s).

In the device depicted in FIGS. 1 and 2, the threaded nut 7 and the coupling sleeve 40 are rotationally constrained to the housing 5 during dose setting or dose correcting, e.g. by means of clicker ratchet 7*a*, 7*b*, whereas the stop wheel 30 rotates relative to the coupling sleeve 40 during dose setting or dose correcting. On the other hand, the threaded nut 7 and the coupling sleeve 40 rotate relative to the housing 5 during dose dispensing, whereas the stop wheel 30 does not rotate relative to the coupling sleeve 40 during dose dispensing. Thus, the respective rotational movements may be used to identify whether the device actually dispenses a dose of medicament. The combination of the signals received from the first detector 21 and the second detector 22 may be used to detect the beginning of dose dispensing and the end of dose dispensing.

The embodiment depicted in FIGS. 1 and 2 features a sensor arrangement 21, 22 located and/or integrated in or on the stop wheel 30 to capture start/stop of rotation, i.e. a motion, the angle of rotation of the stop wheel 30, i.e. the dose size, and the direction of rotation, i.e. whether the rotation increases or decreases (dose correction) the dose. The sensed signals are processed and stored in the data processing unit 20. A rotation protocol is generated which provides information about e.g. the remaining content in the cartridge 3, the dose size or amount of medicament expelled and/or the maximum dose dialed. The data may be queried after each use (injection) and read out via near field communication or an add-on device could read, process and store the data and send the rotation protocol via Bluetooth to another device for further processing. The add-on device may alternatively transmit unprocessed data.

As mentioned above, the feature of a data processing unit 20 using the signals of a first detector 21 and, optionally, a second detector 22 for verifying that a device works in a certain mode may be applied to other drug delivery devices having a component part, like a stop wheel or ring, and a further component part, e.g. a sleeve, performing a certain axial and/or rotational movement only during dose dispensing. Examples for devices into which the data processing unit 20 with the first detector 21 and the second detector 22 may be implemented are disclosed in WO 2014/117944 A1, WO 2016/016184 A1, WO 2017/134131 A1 or in WO 2016/001304 A1.

A further embodiment is depicted in FIGS. 3 and 4, wherein the injection device is essentially similar to that disclosed in EP 2 437 829 B1. FIGS. 3 and 4 show a stop wheel 30 in the form of a threaded last dose nut having external splines 31 for rotationally constraining the stop wheel 30 to the housing (not shown) of the device. Further, FIGS. 3 and 4 show a sleeve 40 in the form of a threaded shaft which is in threaded engagement with the stop wheel 30. The stop wheel 30 is shown in a start position with respect to sleeve 40 in FIG. 3, whereas FIG. 4 shows a position of the stop wheel 30 relative to the sleeve 40 in which the stop wheel 30 abuts and engages a rotational end stop, thereby preventing setting of a dose exceeding the actually set dose.

The stop wheel 30 moves relative to the sleeve 40 during dialling of the injection device due to rotation of the sleeve 40 relative to the housing. However, there is no relative movement between sleeve 40 and stop wheel 30 during dispensing. An additional clicker system 60 is integrated between the sleeve 40 and the stop wheel 30. This clicker system 60 generates a tactile and/or acoustic click signal during dialling of the injection device. One unit of the medicament corresponds to one click generated by clicker system 60. The click noises are detected with the integrated sensor 21. This sensor 21 is located close to the stop wheel 30. This prevents that the signal is disturbed by other noises.

According to this embodiment the positon of the stop wheel 30 (last dose nut) is measured or detected e.g. with a MEMS acceleration sensor. This method may be used for the calculation of the injected doses.

In addition or as an alternative to the device of EP 2 437 829 B1, if there is a relative movement between sleeve 40 and stop wheel 30 during dispensing, the sensor 21 can measure the click signals in addition to dialling click signals. The difference of these counted clicks is the doses size.

REFERENCE NUMERALS 1 cap
2 receptacle
2*a* needle holder
3 cartridge
4 flange
5 housing
6 insert
7 threaded nut
7*a* toothed ring
7*b* spring
8 piston rod
8*a* spline
8*b* thread
9 threaded sleeve
11*a* rotary knob
13 spring
14 button
14*a* stem
data processing unit
21 first detector
22 second detector
30 stop wheel
30*a* cavity
31 splines
40 coupling sleeve
50 dosing sleeve
60 clicker

The invention claimed is:

1. An injection device, comprising:

a housing with a receptacle for a product;

a dosing mechanism for setting a product dosage to be administered and for displaying the set product dosage;

a dispensing mechanism for dispensing the product, the dispensing mechanism comprising a piston rod, which is moveable relative to the housing in a dispensing direction in order to eject the set product dosage in a dispensing stroke corresponding to the set product dosage;

at least one sleeve, which is movable relative to the housing in order to eject the set product dosage;

a stop wheel coupled to the at least one sleeve such that the stop wheel is movable relative to the housing and the at least one sleeve during setting of the product dosage and together with the at least one sleeve relative to the housing during ejection of the set product dosage;

at least a first detector for detecting movement of the stop wheel relative to the housing and/or the at least one sleeve; and a data processing unit connected to the first detector for reading, storing, processing, transmitting, and/or displaying signals received from the first detector;

wherein the first detector and the data processing unit are adapted to detect start and stop of a rotational movement of the stop wheel, an angle of rotation of the rotational movement of the stop wheel, and a direction of the rotational movement of the stop wheel.

2. The injection device according to claim 1, wherein the data processing unit is adapted to provide information about (i) the remaining content in the receptacle, (ii) a dose size and/or an amount of the product ejected from the injection device by the dispensing mechanism, and/or (iii) a maxi-mum dose set by the dosing mechanism based on a rotation protocol containing data received from the first detector.

3. The injection device according to claim 1, wherein the stop wheel comprises at least one cavity and wherein the first detector and/or the data processing unit is received in the at least one cavity.

4. The injection device according to claim 3, wherein the stop wheel comprises an outer skirt with ribs for engaging corresponding inner ribs of a number sleeve of the dosing mechanism and an elastically deformable shaft rotatably mounted in the at least one sleeve, wherein the cavity is an annular space between the outer skirt and the elastically deformable shaft.

5. The injection device according to claim 1, wherein the first detector comprises at least one of an optical sensor, a capacitive sensor, an inductive sensor, a magnetic sensor, or a vibrating structure microelectromechanical systems gyro-scope.

6. The injection device according to claim 1, further comprising a second detector for detecting rotational move-ment of the at least one sleeve or a component part coupled to the at least one sleeve, wherein the data processing unit is connected to the second detector for reading, storing, processing, transmitting, and/or displaying signals received from the second detector.

7. The injection device according to claim 6, wherein the second detector comprises at least one of an optical sensor, a capacitive sensor, an inductive sensor, a magnetic sensor, or a vibrating structure microelectromechanical systems gyroscope.

8. The injection device according to claim 6, wherein the data processing unit is adapted to provide information about the injection device being in a dose setting mode, a dose correction mode, or a dose dispensing mode based on data received from the first detector and the second detector.

9. The injection device according to claim 6, wherein the second detector is located in or on a button of the injection device.

10. The injection device according to claim 1, wherein the data processing unit is connected to at least the first detector via a near field communication or via Bluetooth.

11. The injection device according to claim 1, wherein the data processing unit is adapted to send data to and/or receive data from a separate data processing unit and/or a display device via a near field communication or via Bluetooth.

12. The injection device according to claim 1, further comprising a cartridge containing a medicament.

13. The injection device according to claim 1, wherein the data processing unit is a separate component part provided detachable from the housing.

14. The injection device according to claim 1, further comprising a button, which is moveable relative to the housing and relative to the at least one sleeve in the dispensing direction from a dosing position into a dispensing position in order to eject the set product dosage.

15. The injection device according to claim 1, wherein the stop wheel is an end-of-content stop wheel.

16. The injection device according to claim 1, further comprising a limiting device with a dosing sleeve with a first stop and the stop wheel with a second stop;

wherein the stop wheel follows movements of the dosing sleeve during dosing movements with a defined transmission ratio;

wherein the stop wheel does not move relative to the dosing sleeve during administration processes;

wherein the first stop and the second stop are configured to move through path curves, respectively, such that the first stop and the second stop contact one another in a stop position, whereby a blocking of the movement of the stop wheel and the dosing sleeve relative to each other during dosing movements can be effected; and wherein the path curves are closed and can be moved through multiple times by the first stop, by the second stop or by both the first stop and the second stop until the first stop and the second stop contact one another at the stop position.

17. The injection device according to claim 1, wherein the at least one sleeve is rotationally constrained to the housing during setting of the product dosage and the at least one sleeve is rotatable relative to the housing during ejection of the set product dosage, and wherein the stop wheel is rotatable relative to the housing and the at least one sleeve during setting of the product dosage and together with the at least one sleeve relative to the housing during ejection of the set product dosage.

18. The injection device according to claim 17, wherein the stop wheel is a nut rotationally constrained to the housing and in threaded engagement with the at least one sleeve, wherein the injection device further comprises a clicker mechanism integrated between the stop wheel and the at least one sleeve such that a tactile and/or acoustic click signal is generated during setting of the product dosage, and wherein the first detector is adapted to detect movement of the stop wheel relative to the housing and/or the at least one sleeve by detecting the tactile and/or acoustic click signal generated by the clicker mechanism.

19. The injection device according to claim 1, wherein the at least one sleeve is axially displaceable relative to the housing in order to eject the set product dosage, and wherein the stop wheel is axially displaceable relative to the housing and the at least one sleeve during setting of the product dosage and together with the at least one sleeve relative to the housing during ejection of the set product dosage.

\*   \*   \*   \*   \*